United States Patent
Nemoto et al.

(10) Patent No.: US 11,127,500 B2
(45) Date of Patent: Sep. 21, 2021

(54) CENTRALIZED CONTROL APPARATUS AND DISPLAY CONTROL METHOD OF OPERATION PANEL

(71) Applicant: OLYMPUS CORPORATION, Tokyo (JP)

(72) Inventors: Iori Nemoto, Tokyo (JP); Kiyoshi Sekiguchi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 17/072,534

(22) Filed: Oct. 16, 2020

(65) Prior Publication Data

US 2021/0035684 A1 Feb. 4, 2021

Related U.S. Application Data

(63) Continuation of application No. PCT/JP2019/003126, filed on Jan. 30, 2019.

(30) Foreign Application Priority Data

Apr. 19, 2018 (JP) .............................. JP2018-080722

(51) Int. Cl.
*G16H 40/63* (2018.01)
*A61B 34/00* (2016.01)
(Continued)

(52) U.S. Cl.
CPC ............. *G16H 40/63* (2018.01); *A61B 34/25* (2016.02); *G06F 3/04847* (2013.01); *A61B 2034/254* (2016.02); *G16H 80/00* (2018.01)

(58) Field of Classification Search
CPC ........ G16H 40/63; G16H 80/00; A61B 34/25; A61B 2034/254; A61B 90/00;
(Continued)

(56) References Cited

U.S. PATENT DOCUMENTS

| 10,394,933 B2* | 8/2019 | Putrevu ................. H04L 12/282 |
| 2017/0172674 A1* | 6/2017 | Hanuschik ............. A61B 34/37 |
| 2018/0348968 A1* | 12/2018 | Sasaki ................... G08C 17/00 |

FOREIGN PATENT DOCUMENTS

| JP | 2001-029360 A | 2/2001 |
| JP | 2001-265432 A | 9/2001 |

(Continued)

OTHER PUBLICATIONS

International Search Report dated Apr. 15, 2019 received in PCT/2019/003126.

*Primary Examiner* — Michael Roswell
(74) *Attorney, Agent, or Firm* — Scully, Scott, Murphy & Presser, P.C.

(57) ABSTRACT

A centralized control apparatus includes: an operation panel on which a plurality of operation buttons used to set a plurality of controlled instruments are displayed; and a system controller, the system controller being configured to register the operation buttons, which are displayed when the plurality of controlled instruments satisfy respective operation state conditions, in advance as operation button display conditions, acquire operation states of the plurality of controlled instruments, compare the operation states and the operation state conditions, extract the plurality of operation buttons to be displayed on the operation panel according to a result of the comparison, and display the plurality of extracted operation buttons side by side in time-series order in a predetermined direction of the operation panel.

7 Claims, 9 Drawing Sheets

(51) Int. Cl.
  *G06F 3/0484*   (2013.01)
  *G16H 80/00*   (2018.01)
(58) Field of Classification Search
  CPC ......... A61B 1/045; A61B 18/12; A61B 17/00;
       A61B 1/00; A61B 90/30; G06F 3/04847
  USPC ....................................................... 715/773
  See application file for complete search history.

(56) References Cited

FOREIGN PATENT DOCUMENTS

| | | |
|---|---|---|
| JP | 2004-105533 A | 4/2004 |
| JP | 2006-271885 A | 10/2006 |
| JP | 2017-515522 A | 6/2017 |
| WO | 2015/142933 A1 | 9/2015 |

* cited by examiner

《Switching of operation button due to progress of surgical operation》

| Conditions | Operation buttons to be displayed | Detection methods | Effects |
|---|---|---|---|
| ⟨Batch setting⟩ Execute batch setting | ⟨Electrocautery⟩ Output value UPDOWN button | Detection by controller body | Since the electrocautery is used by gradually increasing output setting after batch setting, it is effective to use the output value UPDOWN button of the electrocautery immediately after execution of the batch setting. |
| ⟨Electrocautery⟩ During output | ⟨Electrocautery⟩ Output value UPDOWN button, Shading display | Read state of electrocautery by communication | It is possible to avoid accidental output risk when electrocautery being used. |
| ⟨Electrocautery⟩ During bipolar output | ⟨Insufflator⟩ Smoke exhaust button | Read state of electrocautery by communication | Since you want to exhaust smoke emitted from an abdominal cavity during a bipolar output with an insufflator, it is effective to use the smoke exhaust button immediately. |
| ⟨Electrocautery⟩ After output | ⟨Electrocautery⟩ Monopolar output value UPDOWN button | Read state of electrocautery by communication | Since the electrocautery is used by changing output setting depending on a specific cut of an affected part, it is effective to use the output value UPDOWN button of the electrocautery immediately after output. |
| ⟨Electrocautery⟩ After output | ⟨Processor⟩ Zoom UPDOWN button | Read state of electrocautery by communication | Since confirmation is performed by zoom-up of a treatment portion during output of electrocautery, it is effective to use the zoom-UP button immediately. |
| ⟨Processor⟩ White balance execution of endoscope | ⟨Recorder⟩ Recording start button | Read state of endoscope apparatus by communication | After the white balance is executed, the endoscope observation starts, and thus the recording is executed. Therefore, it is effective to use the recording button immediately. |
| ⟨Shadowless light⟩ Lighting | ⟨Electrocautery⟩ Monopolar output value UPDOWN button | Read state of shadowless light by communication | After the shadowless light is turned on, an abdominal incision by the monopolar starts, so it is effective to use the output value UPDOWN button immediately. |
| ⟨Shadowless light⟩ Lighting | ⟨Indoor light⟩ ON/OFF button | Read state of shadowless light by communication | After the shadowless light is turned on, the procedure starts, so it is effective to use the indoor light ON/OFF button immediately. |
| ⟨Shadowless light⟩ Lighting | ⟨Light source⟩ ON/OFF button | Read state of shadowless light by communication | After the shadowless light is turned on, the procedure starts, so it is effective to use the light source ON/OFF button immediately. |

FIG. 4

《Switching of operation button due to occurrence of abnormality》

| Conditions | Operation buttons to be displayed | Detection methods | Effects |
|---|---|---|---|
| Gas cylinder empty error | Phone button | Read state of insufflator by communication | When the gas cylinder is empty, since you will make a call to bring a replacement gas cylinder, it is effective to use the phone button immediately. |
| DVD remaining-amount error | Phone button | Read state of recorder by communication | When the DVD is empty, since you will make a call to bring a replacement DVD, it is effective to use the phone button immediately. |
| Large amount of bleeding | Electrocautery coagulation output value UPDOWN button | Measure the amount of red in an endoscopic image by image processing | When a large amount of bleeding occurs, coagulation output is performed to stop bleeding, so it is effective to use the coagulation output value UPDOWN button immediately. |
| Complications due to injection of carbon dioxide | Abdominal gas UPDOWN button | Measure blood gas concentration with vital sign monitor | In order to lower the abdominal gas pressure when the blood gas concentration rises, it is effective to use the abdominal gas pressure UPDOWN button immediately. |
| Failed to set patient ID in video system center | Inspection end execution button | Read state of video system center by communication | When the setting of the patient ID fails, since the inspection is ended and the patient ID is set again, it is effective to use the inspection end button immediately. |
| Failed to set patient ID in image recording apparatus | Folder close button | Read state of image recording apparatus by communication | When the setting of the patient ID fails, since the folder is closed to set the patient ID again, it is effective to use the folder close button immediately. |
| 2D/3D settings do not match between 3D monitor and video system center | 2D/3D settings button between 3D monitor and video system center | Read state of 3D monitor and video system center | When 2D/3D settings between 3D monitor and video system center do not match each other, a correct image is not displayed, so it is effective to use the 2D/3D settings button immediately |

CENTRALIZED CONTROL APPARATUS AND DISPLAY CONTROL METHOD OF OPERATION PANEL

CROSS REFERENCE TO RELATED APPLICATION

This application is a continuation application of PCT/JP2019/003126 filed on Jan. 30, 2019 and claims benefit of Japanese Application No. 2018-080722 filed in Japan on Apr. 19, 2018, the entire contents of which are incorporated herein by this reference.

BACKGROUND OF THE INVENTION

1. Field of the Invention

Embodiments of the present invention relate to a centralized control apparatus and a display control method of an operation panel that intensively control a plurality of medical instruments and equipment instruments in a surgical operation.

2. Description of the Related Art

In recent years, with advances in technology, there have been a wide variety of medical instruments, for example, endoscopes used to pick up a medical image and insufflation apparatuses used to insufflate an abdominal cavity of a patient, and functions of the medical instruments have been enhanced. In addition to such medical instruments, various equipment instruments such as room lights, various display apparatuses, and recording apparatuses are disposed in an operating room. When such instruments are operated individually, the work becomes complicated and the procedure time is delayed. In order to address such drawback, centralized control apparatuses (system controllers) for intensively controlling and managing the medical instruments and the equipment instruments have been developed and put into practical use in recent years (see Japanese Patent Application Laid-Open Publication No. 2004-105533, for example).

In a general surgical operation, a nurse in a sterilized area in the operating room operates an input apparatus such as an operation panel connected to a system controller each time various scene changes are made during the surgical operation, and thus on/off and setting change of various connected instruments are performed.

SUMMARY OF THE INVENTION

A centralized control apparatus according to one aspect of the present invention includes: an operation panel provided with a plurality of display areas in which a plurality of operation buttons are displayed, respectively, the plurality of operation buttons being used to set and input operations for a plurality of controlled instruments; and a system controller, the system controller being configured to register the plurality of operation buttons in advance as operation button display conditions, the plurality of operation buttons being displayed on the operation panel when the plurality of controlled instruments satisfy respective predetermined operation state conditions, acquire operation states of the plurality of controlled instruments used in a procedure, compare the operation states of the plurality of controlled instruments with the operation state conditions of the plurality of controlled instrument registered as the operation button display conditions, extract the plurality of operation buttons to be displayed on the operation panel according to a result of the comparison, and display the plurality of extracted operation buttons side by side in time-series order in a predetermined direction of the operation panel.

A display control method of an operation panel according to another aspect of the present invention includes: registering a plurality of operation buttons in advance as operation button display conditions, the plurality of operation buttons being displayed on the operation panel when a plurality of controlled instruments satisfy respective predetermined operation state conditions and used to set an operation for each of the plurality of controlled instruments; acquiring operation states of the plurality of controlled instruments used in a procedure; comparing the operation states with the operation state conditions registered as the operation button display conditions; extracting the plurality of operation buttons to be displayed on the operation panel according to a result of the comparison; and disposing and displaying the plurality of operation buttons on the operation panel according to a result of the extraction.

A display control method of an operation panel according to further another aspect of the present invention includes: registering a plurality of operation buttons in advance as operation button display conditions, the plurality of operation buttons being displayed on the operation panel when a plurality of controlled instruments satisfy respective predetermined operation state conditions and used to set an operation for each of the plurality of controlled instruments; acquiring operation states of the plurality of controlled instruments used in a procedure; comparing the operation states with the operation state conditions registered as the operation button display conditions; extracting the plurality of operation buttons to be displayed on the operation panel according to a result of the comparison; and displaying the plurality of operation buttons side by side in time-series order in a predetermined direction of the operation panel according to a result of the extraction, the operation panel being provided with a plurality of display areas in which the plurality of operation buttons are displayed, respectively.

BRIEF DESCRIPTION OF THE DRAWINGS

FIG. 3 is a view illustrating an example of display conditions of operation buttons;

FIG. 4 is a view illustrating an example of display conditions of operation buttons;

DETAILED DESCRIPTION OF THE PREFERRED EMBODIMENT

An embodiment will be described below with reference to the drawings.

Figure 1:
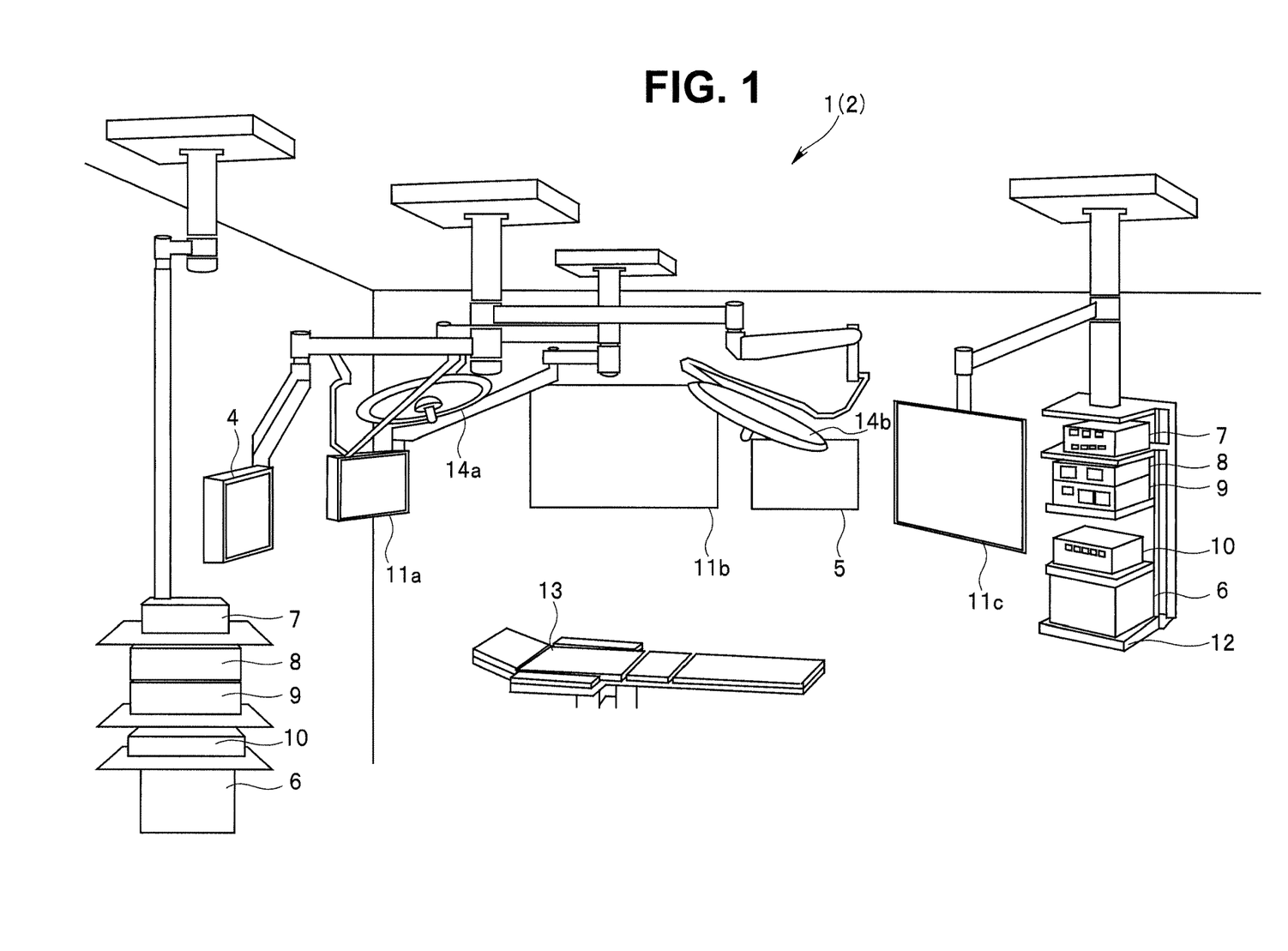
FIG. 1 is a diagram illustrating an example of an overall configuration of a medical system including a centralized control apparatus according to an embodiment of the present invention.

FIG. 1 is a diagram illustrating an example of an overall configuration of a medical system including a centralized control apparatus according to an embodiment of the present invention. As shown in FIG. 1, a medical system 1 of the present embodiment includes a peripheral instrument 2 that is a controlled instrument including a plurality of medical instruments, an operation panel 4 that receives an operation from an operator such as a nurse, a display panel 5, and a system controller 6 that is a centralized control apparatus configured to intensively control the peripheral instrument 2.

The peripheral instrument 2 includes a plurality of medical instruments that performs observation, inspection, and treatment. Specifically, the peripheral instrument 2 includes a camera apparatus for endoscope 7, an insufflation apparatus 8, a light source apparatus 9, an electrocautery apparatus 10, and monitors (monitor 11a, monitor 11b, and monitor 11c). The peripheral instrument 2 is not limited to these medical instruments, and may include a recording apparatus, for example.

Figure 5:
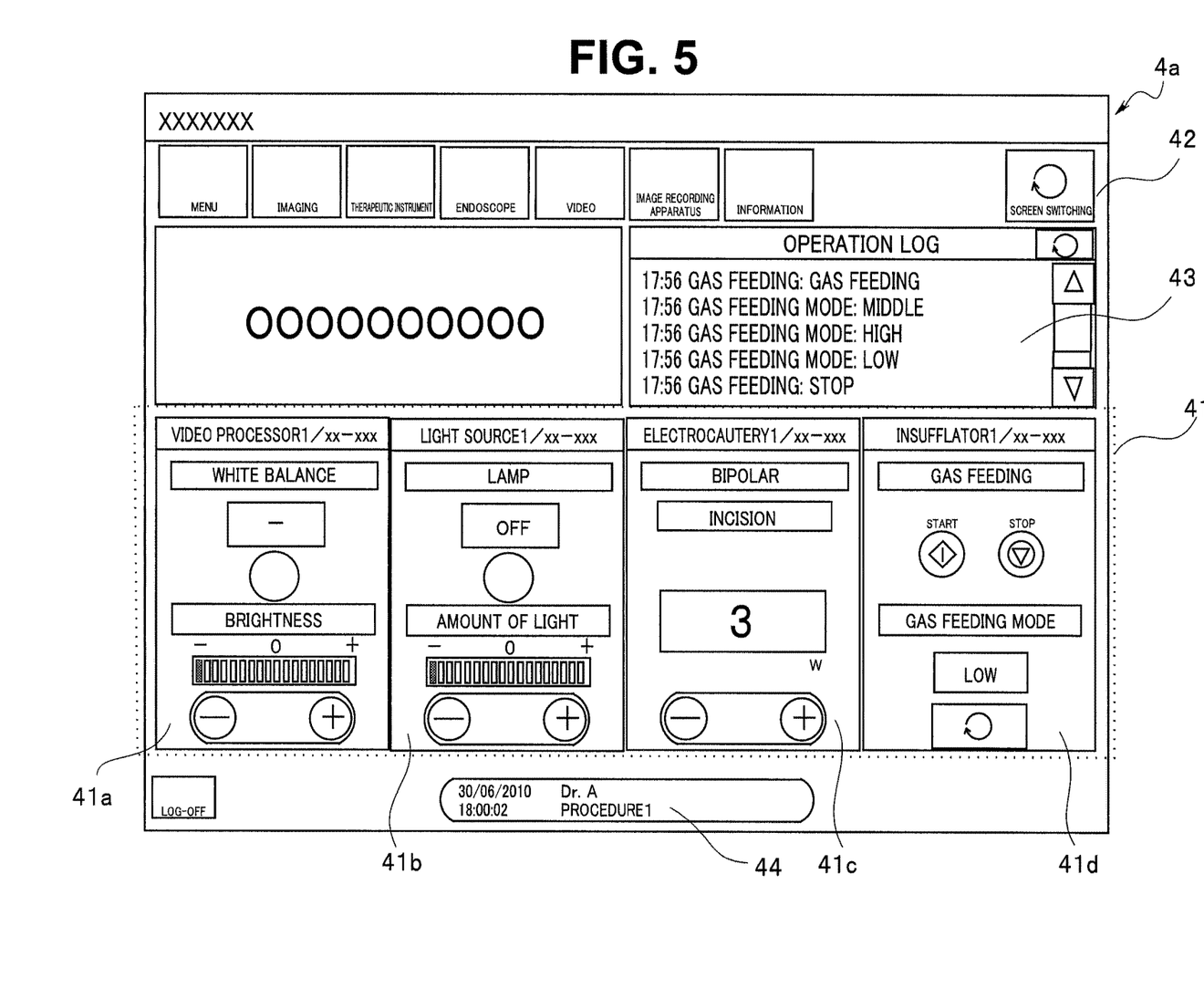
FIG. 5 is a view illustrating an example of a configuration of an operation screen on an operation panel.

The operation panel 4 is, for example, a touch panel display in which a liquid crystal display and a touch panel sensor disposed by overlapping on the liquid crystal display are integrally configured. The operation panel 4 is an apparatus that receives an operation from, for example, a nurse in a non-sterilized region to operate the peripheral instrument 2, and operation information is inputted to the system controller 6. The display panel 5 is display means capable of selectively displaying all data during a surgical operation.

The light source apparatus 9 is connected to an endoscope (not shown) via a light guide cable through which illumination light is transmitted. The illumination light transmitted from the light source apparatus 9 is supplied to the endoscope to illuminate an affected part in an abdomen of a patient into which an insertion portion of the endoscope is inserted.

A camera head provided with an image pickup device is attached to a proximal end side of the insertion portion of the endoscope, and an optical image of the affected part is picked up by the image pickup device provided in the camera head. An image pickup signal picked up by the image pickup device is transmitted to the camera apparatus for endoscope 7 through a cable.

The camera apparatus for endoscope 7 performs predetermined signal processing on the transmitted image pickup signal to generate a video signal. Then, the camera apparatus for endoscope 7 outputs the generated video signal to the monitor 11a, the monitor 11b, and the monitor 11c via the system controller 6. The inputted video signal, that is, the endoscope image of the affected part is displayed on the monitors 11a and 11c hung from a ceiling and the monitor 11b attached to a wall.

A carbon dioxide cylinder (not shown) is connected to the insufflation apparatus 8, and carbon dioxide gas is supplied into the abdomen of the patient through an insufflation tube extending from the insufflation apparatus 8 to the patient.

The system controller 6, the camera apparatus for endoscope 7, the insufflation apparatus 8, the light source apparatus 9, and the electrocautery apparatus 10 are installed in a rack 12. The system controller 6 controls not only the peripheral instrument 2 described above but also equipment instruments installed in an operating room, as controlled instruments, the equipment instruments also serving as the peripheral instrument 2 and including a bed for patient 13 on which the patient lies, a shadowless light (a shadowless light 14a or a shadowless light 14b) hung from the ceiling, and an indoor light (not shown). In FIG. 1, for example, assuming a surgical operation using the endoscope and a laparoscope, two sets are provided, one set including the system controller 6, the camera apparatus for endoscope 7, the insufflation apparatus 8, the light source apparatus 9, and the electrocautery apparatus 10, but only one set may be provided, or three or more sets may be provided.

Although FIG. 1 illustrates the medical system 1 installed in the operating room where a surgical operation is performed under the endoscope, the medical system 1 is not limited to the use of the surgical operation under the endoscope, and may be used for other surgical operations and medical examinations. In addition, the medical system 1 may be provided in a room such as a medical examination room other than the operating room. The medical system 1 may further include various apparatuses and equipment which are not shown in FIG. 1. For example, the medical system 1 may include a surgical field camera used to observe a surgical field, and may control these apparatuses and equipment using the system controller 6.

Figure 2:
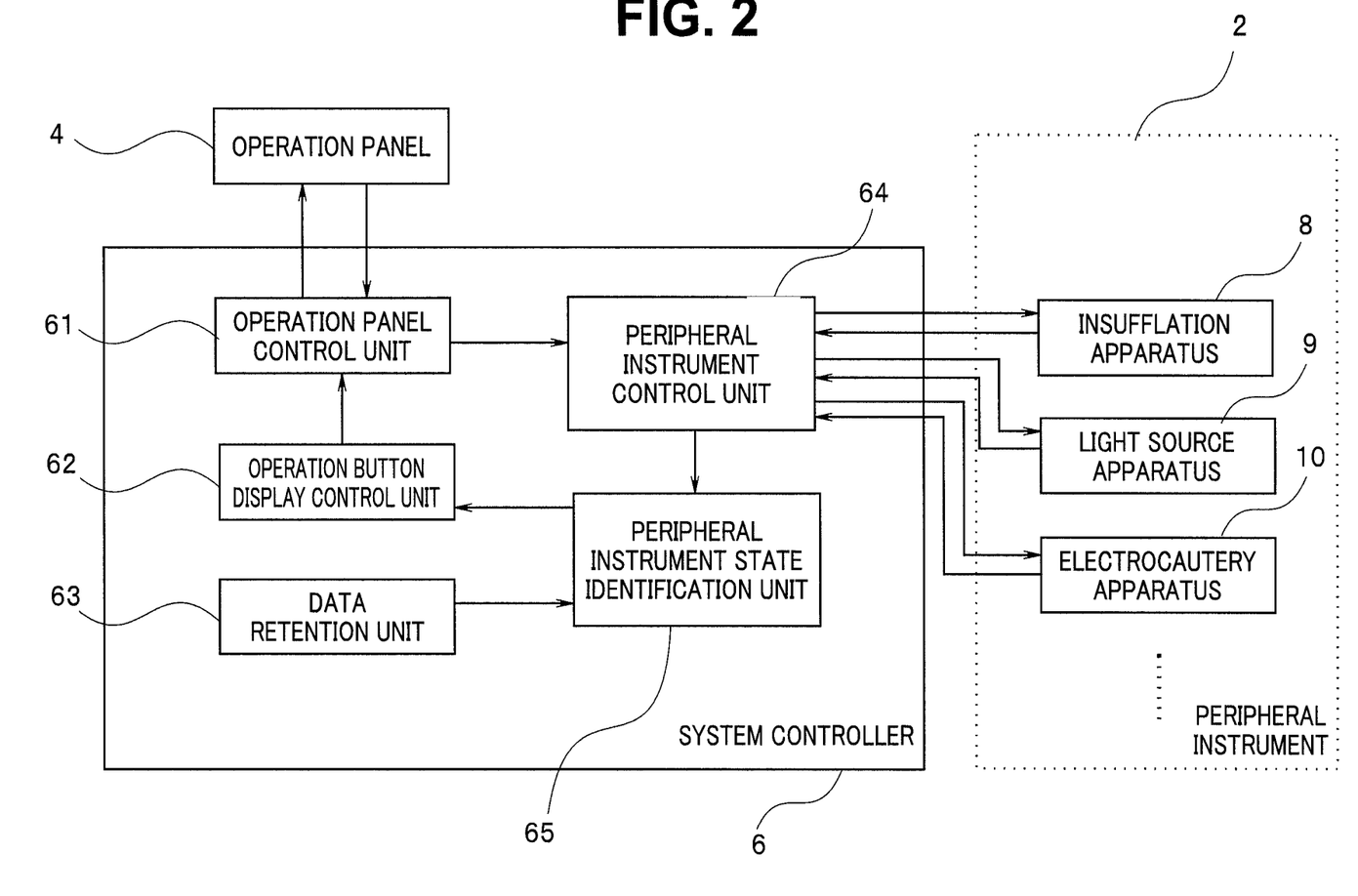
FIG. 2 is a schematic block diagram illustrating a configuration of a system controller.

A detailed configuration of the system controller 6 will be described below. FIG. 2 is a schematic block diagram illustrating an example of the configuration of the system controller. As shown in FIG. 2, the peripheral instrument 2 serving as a controlled instrument and the operation panel 4 serving as an input apparatus of the operation are connected to the system controller 6.

The system controller 6 includes an operation panel control unit 61, an operation button display control unit 62, a data retention unit 63, a peripheral instrument control unit 64, and a peripheral instrument state identification unit 65.

At least one of the plurality of components (the operation panel identification unit 61, the operation button display control unit 62, the data retention unit 63, the peripheral instrument control unit 64, and the peripheral instrument state control unit 65) of the system controller 6 may be composed of a processor that operates by software, or may be composed of hardware.

The operation panel control unit 61 receives control signals, such as on/off of the peripheral instrument and change of set values, which are inputted by a press of the operation panel 4. The received control signals are outputted to the peripheral instrument control unit 64. Further, an operation screen 4a (see FIG. 5) used to operate the peripheral instrument is outputted to the operation panel 4 to be displayed.

The peripheral instrument control unit 64, which is an operation state acquisition unit, acquires various data and setting parameters indicating operation states of the respective instruments from the peripheral instrument 2, which is connected to the system controller 6 and can be intensively controlled, and outputs such data and parameters to the peripheral instrument state identification unit 65. In addition, the peripheral instrument control unit 64 outputs the control signal inputted from the operation panel control unit 61 and used to operate the peripheral instrument 2 to the peripheral instrument 2, and changes the state of the peripheral instrument 2.

The peripheral instrument state identification unit 65, which is an operation button identification unit, compares the state of the peripheral instrument 2 inputted from the peripheral instrument control unit 64 with operation button display conditions, and determines an operation button to be displayed on the operation screen 4a. The operation button display conditions are registered in advance in the data retention unit 63, which is a condition registration unit, and is read into the peripheral instrument state identification unit 65 as needed. Information on the determined operation button is outputted to the operation button display control unit 62.

FIGS. 3 and 4 shows an example of operation button display conditions of a plurality of peripheral instruments 2. FIG. 3 shows an example of conditions for switching the operation button as the surgical operation progresses, and FIG. 4 shows an example of conditions for switching the operation button due to occurrence of an abnormality. The operation button display conditions include three items: "Condition" for switching the operation button, "Operation button" for displaying when the state of the peripheral instrument matches the condition, and "Detection method" for detecting the condition.

FIGS. 3 and 4 also show "Effect" obtained by switching the operation buttons according to the operation button display conditions of the plurality of peripheral instruments 2. The "Effect" item is used as a reference at the time of reviewing or changing the table of operation button display conditions, and the content itself does not directly contribute to switching conditions or switching operations of the operation buttons.

For example, when the state of the electrocautery apparatus 10 changes and the output is started, the operation state matches "during output of electrocautery" which is a condition on a second line in FIG. 3. Therefore, the operation button to be displayed on the operation screen 4a is selected according to the content described in the "operation button" on a second line, and is instructed to the operation button display control unit 62. In other words, an instruction is transmitted to the operation button display control unit 62 to perform a shading display on a button (output value UPDOWN button) used to change an output value of the electrocautery apparatus 10.

In addition, for example, when it is detected that the state of the insufflation apparatus 8 changes and the gas cylinder has become empty, the operation state matches a "gas cylinder empty error" which is a condition on a first line in FIG. 4. Therefore, the operation button to be displayed on the operation screen is selected according to the content described in the "operation button" on a first line, and is instructed to the operation button display control unit 62. In other words, an instruction is transmitted to the operation button display control unit 62 to display a phone button used to start communication with the outside of the operating room by phone.

The operation button display control unit 62 selects an operation button to be displayed on the operation screen 4a according to the instruction content inputted from the peripheral instrument state identification unit 65, and outputs the selected operation button and the display conditions (for example, a normal display and a shading display) of the operation button to the operation panel control unit 61. The operation panel control unit 61 generates an operation screen 4a to be displayed on the operation panel 4 according to the display conditions of the operation button inputted from the operation button display control unit 62. The generated operation screen 4a is outputted to the operation panel 4 to be displayed.

The configuration of the operation screen 4a will be described with reference to FIG. 5. FIG. 5 is a view illustrating an example of the configuration of the operation screen on the operation panel. As shown in FIG. 5, an operation button display area 41 as an operation instruction area used to instruct an operation on the peripheral instrument 2 is disposed on the operation screen 4a.

Further, the operation screen 4a is provided with a screen switching button display area 42 in which a screen switching button for switching a screen itself to be displayed on the operation panel 4 is disposed, an operation log display area 43 used to display information on various operations executed by the peripheral instrument 2 up to that time, and a surgical operation information display area 44 used to display information on a surgical operation currently being performed, for example, a name of the surgical operation.

The operation button display area 41 is provided with operation instruction areas 41a, 41b, 41c, and 41d in which the operation buttons used to instruct the operation on the peripheral instrument 2 are disposed. In other words, in the case of the example shown in FIG. 5, operation buttons used to operate up to four peripheral instruments 2 can be disposed on the operation screen 4a. In the operation instruction areas 41a, 41b, 41c, and 41d, any one of the operation buttons set in the "Operation button" item of the operation button display condition is selected and disposed. In FIG. 5, as an example, operation buttons related to a video processor, which is the camera apparatus for endoscope 7, are disposed in the operation instruction area 41a, and operation buttons related to the light source apparatus 9 are disposed in the operation instruction area 41b. Further, operation buttons related to the electrocautery apparatus 10 are disposed in the operation instruction area 41c, and operation buttons related to the insufflation apparatus 8 are disposed in the operation instruction area 41d.

The number of operation instruction areas 41a, 41b, 41c, and 41d to be disposed on the operation screen 4a is not limited to four, and a necessary number can be disposed.

Further, the operation buttons need not to be displayed in all of the operation instruction areas 41a, 41b, 41c, and 41d, and the operation buttons related to only the peripheral instrument 2, which requires the operation, are disposed according to the instruction of the system controller 6. For example, when the operation on the peripheral instrument 2 is not required, all of the operation instruction areas 41a, 41b, 41c, and 41d are in a blank state in which nothing is displayed.

A layout of the operation screen 4a is not limited to the layout shown in FIG. 5. For example, the operation button display area 41 may not be disposed at a lower half of the screen, and four operation instruction areas 41a, 41b, 41c, and 41d may not be displayed side by side. For example, a left half of the operation screen 4a is used as the operation button display area 41, the area is divided into two parts in a horizontal direction and a vertical direction to create four areas, and the operation instruction areas 41a, 41b, 41c, and 41d may be disposed in the four areas, respectively. Further, the display contents other than the operation button display area 41 on the operation screen 4a are not also limited to the screen switching button display area 42, the operation log display area 43, and the surgical operation information display area 44, and other contents may be displayed or an area may exist which is not displayed.

Figure 6:
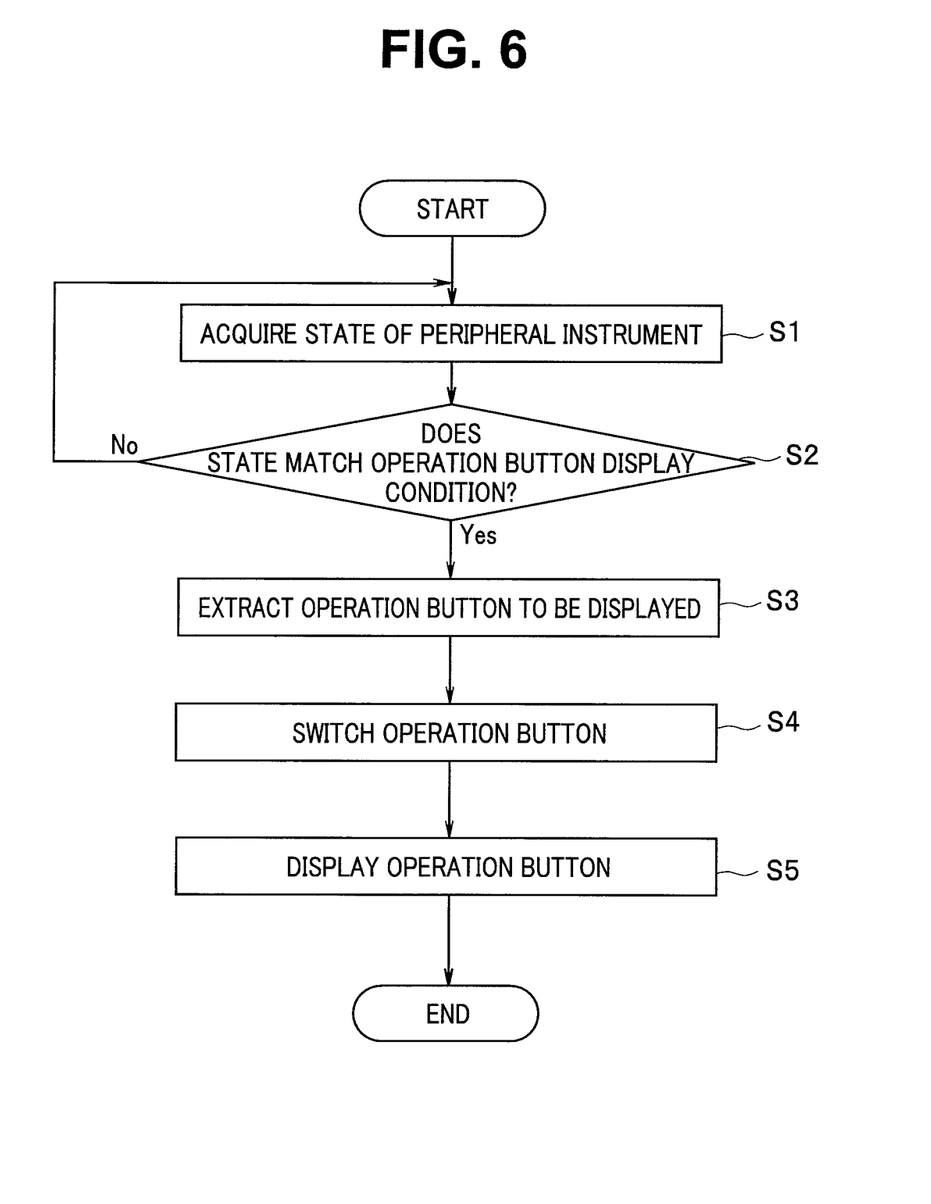
FIG. 6 is a flowchart illustrating an example of a display control procedure for operation buttons.

An operation button display control operation of the system controller 6 in the present embodiment will be described with reference to FIG. 6. FIG. 6 is a flowchart illustrating an example of a display control procedure for operation buttons.

First, when the power of the system controller 6 is turned on and initial setting is completed, the peripheral instrument control unit 64 acquires operation states of various peripheral instruments 2 being connected (S1). Specifically, the peripheral instrument control unit 64 acquires output information as an operation state, via methods or communication paths corresponding to the individual peripheral instruments 2, according to the method described in the "Detection method" item such that the content set in the "Condition" item of the operation button display condition can be determined. For example, the peripheral instrument control unit 64 acquires output information of the electrocautery apparatus 10, processing execution information in the camera apparatus for endoscope 7, lighting/extinguishing state information of the shadowless lights 14a and 14b, and remaining amount information in the gas cylinder of the insufflation apparatus 8. The peripheral instrument control unit 64 outputs the acquired operation information of the peripheral instrument 2 to the peripheral instrument state identification unit 65.

Next, the peripheral instrument state identification unit 65 reads the operation button display condition from the data retention unit 63, and compares the acquired operation state of the peripheral instrument 2 with the contents set in the "Condition" item of the same display condition (S2). When the matching condition is not extracted (No in S2), the process returns to S1, and the state of the peripheral instrument 2 is acquired.

On the other hand, when the matching condition is extracted (Yes in S2), the peripheral instrument state identification unit 65 extracts the content, which is described in the "Operation button" item, corresponding to the extracted condition (S3). For example, when the shadowless lights 14a and 14b are turned on, the operation state matches a condition "lighting of the shadowless light" on a seventh line of the operation button display condition shown in FIG. 3. Therefore, the peripheral instrument state identification unit 65 extracts the content set in "operation button" on a seventh line, that is, a monopolar output UPDOWN button of the electrocautery apparatus 10. Then, the peripheral instrument state identification unit 65 instructs the operation button display control unit 62 to display the extracted operation button.

Subsequently, the operation button display control unit 62 selects the instructed operation button, and sets the selected operation button and the display condition (for example, the normal display and the shading display) of the operation button in the operation panel control unit 61 (S4). In the case of the example described above, the operation button display control unit 62 sets the operation panel control unit 61 to normally display the monopolar output UPDOWN button of the electrocautery apparatus 10.

The operation button display area 41 of the operation screen 4a is set such that newly selected operation buttons are displayed in the order of the operation instruction areas 41a, 41b, 41c, and 41d. In other words, when all of the operation instruction areas 41a, 41b, 41c, and 41d are in a blank state and the operation buttons are not disposed, the operation buttons newly selected by the operation button display control unit 62 are set to be displayed in the operation instruction area 41a. In addition, when the operation buttons are already disposed in the operation instruction area 41a, the display positions of the operation buttons are moved to the operation instruction area 41b, and then the newly selected operation buttons are set to be displayed in the operation instruction area 41a.

When the operation buttons are already disposed in all of the operation instruction areas 41a, 41b, 41c, and 41d, the operation button disposed in the operation instruction area 41d and displayed for the longest time is deleted, the display positions of the operation buttons disposed in the operation instruction area 41c are moved to the operation instruction area 41d, the display positions of the operation buttons disposed in the operation instruction area 41b are moved to the operation instruction area 41c, the display positions of the operation buttons disposed in the operation instruction area 41a are moved to the operation instruction area 41b, and then the newly selected operation buttons are set to be displayed in the operation instruction area 41a. In other words, the plurality of operation buttons are displayed side by side in a predetermined direction of the operation panel in time-series order.

When the newly selected operation buttons are always displayed in the operation instruction area 41a in this way, since the operation buttons that need to be operated according to the state change of the peripheral instrument 2 are always displayed at the same position, user's convenience is improved and operation efficiency is improved.

Subsequently, the operation panel control unit 61 generates an operation screen 4a to be displayed on the operation panel 4 according to the display conditions of the operation buttons inputted from the operation button display control unit 62, and the generated operation screen 4a is outputted to the operation panel 4 to be displayed (S5).

Figure 7:
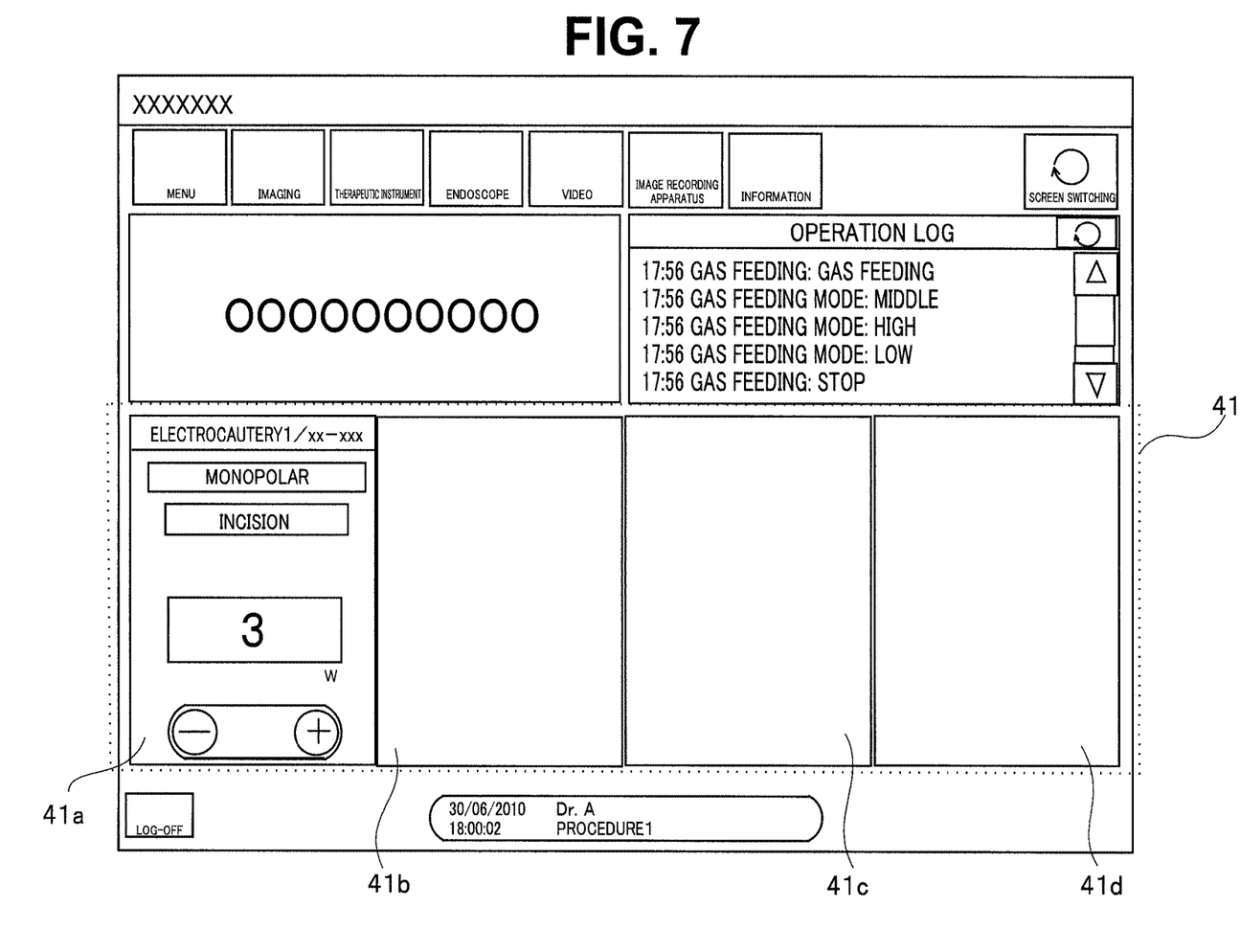
FIG. 7 is a view illustrating an example of an operation screen on the operation panel.
Figure 8:
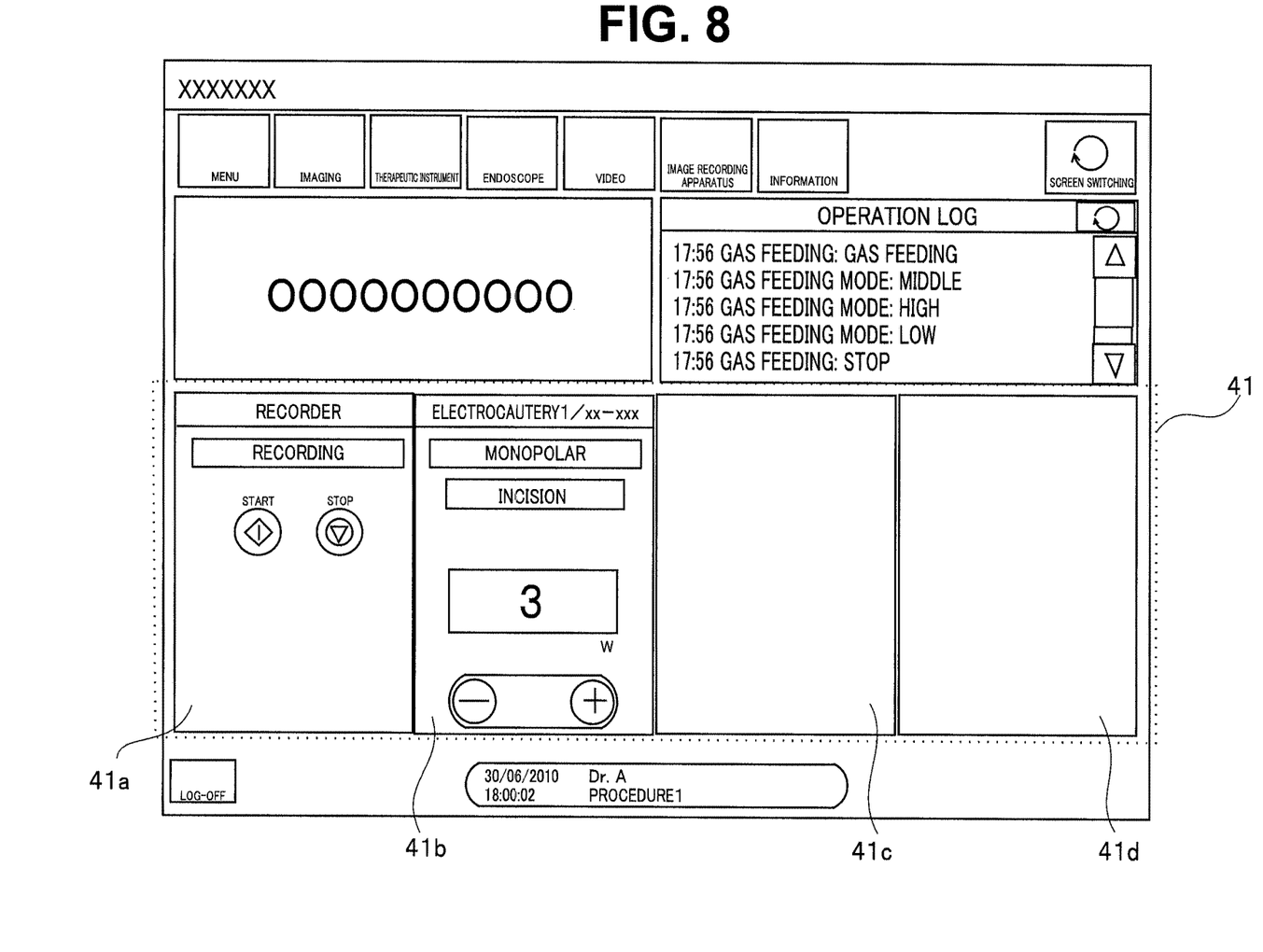
FIG. 8 is a view illustrating an example of an operation screen on the operation panel.
Figure 9:
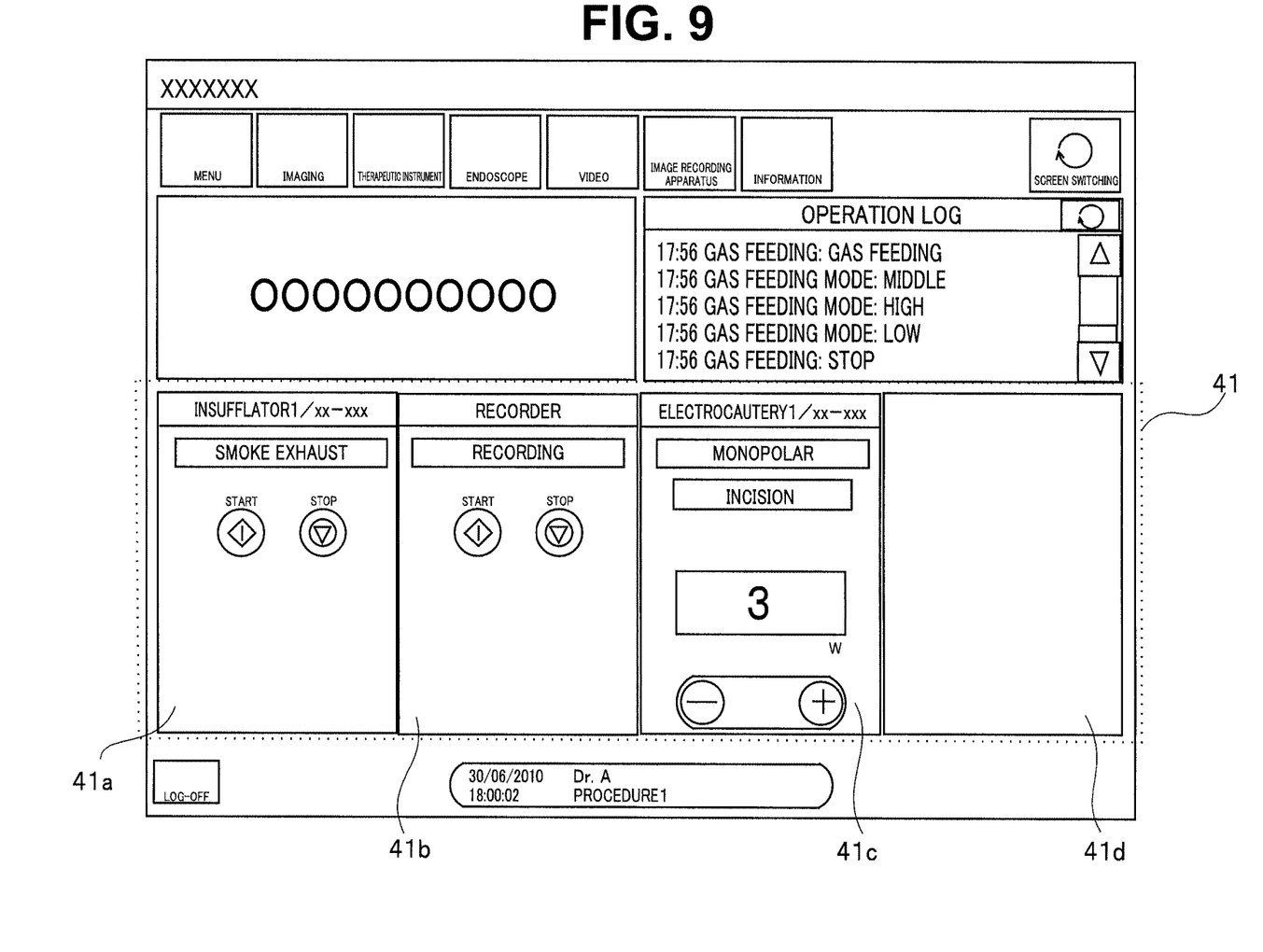
FIG. 9 is a view illustrating an example of an operation screen on the operation panel.

FIGS. 7 to 9 are views illustrating examples of the operation screen of the operation panel. For example, similarly to the example described above, when the display of the monopolar output UPDOWN button of the electrocautery apparatus 10 is set in a state where the operation buttons is not disposed in the operation instruction area 41a, the monopolar output UPDOWN button of the electrocautery apparatus 10 is displayed in the operation instruction area 41a and three areas of the operation instruction areas 41b, 41c, and 41d are in a blank state as shown in FIG. 7.

When the update of the display on the operation panel 4 is completed in S5, the process returns to S1 until the procedure is completed, the display control operation is continuously performed to periodically acquire the state of the peripheral instrument 2 and automatically display the operation buttons according to situations.

For example, when the end of the output of the electrocautery apparatus 10 is detected after the shadowless lights 14a and 14b are turned on, it is determined in S2 that the operation state matches a condition on a fourth line of the operation button display condition shown in FIG. 3. Therefore, the peripheral instrument state identification unit 65 extracts the content set in "operation button" on a sixth line, that is, a monopolar output UPDOWN button of the electrocautery apparatus 10. Then, the peripheral instrument state identification unit 65 instructs operation button display control unit 62 of the extracted operation button (S3).

The operation button display control unit 62 selects the monopolar output UPDOWN button of the electrocautery apparatus 10 (S4). At this time, the monopolar output UPDOWN button of the electrocautery apparatus 10 is already displayed in the operation instruction area 41a. When the same operation button as the operation button displayed immediately before is selected, the operation screen 4a continuously maintains the original state without being updated. In other words, the operation panel control unit 61 gives a display instruction to the operation panel 4 without changing the operation screen 4a to be displayed on the operation panel 4 (S5).

When a white balance is executed in the camera apparatus for endoscope 7 after the end of the output of the electrocautery apparatus 10 is detected, it is determined in S2 that the operation state matches the condition on the sixth line of the operation button display condition shown in FIG. 3. Therefore, the peripheral instrument state identification unit 65 extracts the content set in the "operation button" on a sixth line, that is, a recording start button of the recording apparatus. Then, the peripheral instrument state identification unit 65 instructs the operation button display control unit 62 of the extracted operation button (S3).

The operation button display control unit 62 selects the recording start button of the recording apparatus, and sets the operation panel control unit 61 to normally display the operation button (S4). At this time, the monopolar output UPDOWN button of the electrocautery apparatus 10 is already displayed in the operation instruction area 41a. Therefore, the operation button display control unit 62 moves the display position of the monopolar output UPDOWN button of the electrocautery apparatus 10 to the operation instruction area 41b, and sets the operation instruction area 41a to display the recording start button of the recording apparatus.

Subsequently, the operation panel control unit 61 generates an operation screen 4a to be displayed on the operation panel 4 according to the display conditions of the operation buttons inputted from the operation button display control unit 62, and the generated operation screen 4a is outputted to the operation panel 4 to be displayed (S5). In the above-described case, the operation screen 4a is displayed on the operation panel 4 as shown in FIG. 8.

Thereafter, when a bipolar output is detected in the electrocautery apparatus 10, it is determined in S2 that the operation state matches a condition on a third line of the operation button display condition shown in FIG. 3. Therefore, the peripheral instrument state identification unit 65 extracts the content set in the "operation button" on a third line, that is, a smoke exhaust button of the insufflation apparatus 8. Then, the peripheral instrument state identification unit 65 instructs the operation button display control unit 62 of the extracted operation button (S3).

The operation button display control unit 62 selects the smoke exhaust button of the insufflation apparatus 8, and sets the operation panel control unit 61 to normally display the operation button (S4). At this time, the recording start button of the recording apparatus is already displayed in the operation instruction area 41a. Further, the monopolar output UPDOWN button of the electrocautery apparatus 10 is already displayed in the operation instruction area 41b. Therefore, the operation button display control unit 62 moves the display position of the monopolar output UPDOWN button of the electrocautery apparatus 10 to the operation instruction area 41c, moves the display position of the recording start button of the recording apparatus to the operation instruction area 41b, and then sets the operation instruction area 41a to display the smoke exhaust button of the insufflation apparatus 8.

Subsequently, the operation panel control unit 61 generates an operation screen 4a to be displayed on the operation panel 4 according to the display conditions of the operation buttons inputted from the operation button display control unit 62, and the generated operation screen 4a is outputted to the operation panel 4 to be displayed (S5). In the above-described case, the operation screen 4a is displayed on the operation panel 4 as shown in FIG. 9.

As described above, according to the present embodiment, when the state (both the normal state and the abnormal state) of the peripheral instrument 2 serving as a controlled instrument satisfies a predetermined condition, the operation buttons to be displayed on the operation screen 4a are registered in advance as an operation button condition. When the state of the peripheral instrument 2 is periodically acquired and matches the operation button condition by comparison, the registered operation buttons are automatically displayed on the operation screen 4a. Accordingly, predetermined operation buttons of the peripheral instrument, which need to be controlled, are automatically displayed on the operation panel 4 according to the progress of the procedure or during the occurrence of the abnormality. Therefore, it is not necessary to search for the operation button and call it on the screen, and it is possible to quickly perform the operation of the peripheral instrument and prevent the delay of the progress of the surgical operation.

Although some embodiments of the present invention have been described, these embodiments are exemplary by way of example and are not intended to limit the scope of the invention. These novel embodiments can be implemented in various other forms, and various omissions, replacements, and changes can be made without departing from the gist of the invention. These embodiments and modifications thereof are included in the scope and gist of the invention, and are also included in the scope of the invention described in the claims and the equivalent scope thereof.

What is claimed is:

1. A centralized control apparatus comprising:
an operation panel provided with a plurality of display areas in which a plurality of operation buttons are displayed, respectively, the plurality of operation buttons being used to set and input operations for a plurality of controlled instruments; and
a system controller,
the system controller being configured to
register the plurality of operation buttons in advance as operation button display conditions, the plurality of operation buttons being displayed on the operation panel when the plurality of controlled instruments satisfy respective predetermined operation state conditions,
acquire operation states of the plurality of controlled instruments used in a procedure,
compare the operation states of the plurality of controlled instruments with the operation state conditions of the plurality of controlled instrument registered as the operation button display conditions,
extract the plurality of operation buttons to be displayed on the operation panel according to a result of the comparison, and
display the plurality of extracted operation buttons side by side in time-series order in a predetermined direction of the operation panel.

2. The centralized control apparatus according to claim 1, wherein when an operation button to be displayed subsequently is determined in a case where an operation button is displayed in each of the plurality of display areas of the operation panel, the system controller deletes an operation button displayed on the operation panel for a longest time.

3. The centralized control apparatus according to claim 1, wherein the system controller acquires, as the operation states, output information of the plurality of controlled instruments, the output information changing according to a progress of the procedure.

4. The centralized control apparatus according to claim 1, wherein the system controller acquires, as the operation states, abnormal states that occur during a progress of the procedure.

5. The centralized control apparatus according to claim 1, wherein the plurality of controlled instruments include medical instruments used in the procedure and equipment instruments installed in an environment in which the procedure is performed.

6. A display control method of an operation panel comprising:
  registering a plurality of operation buttons in advance as operation button display conditions, the plurality of operation buttons being displayed on the operation panel when a plurality of controlled instruments satisfy respective predetermined operation state conditions and used to set an operation for each of the plurality of controlled instruments;
  acquiring operation states of the plurality of controlled instruments used in a procedure;
  comparing the operation states with the operation state conditions registered as the operation button display conditions;
  extracting the plurality of operation buttons to be displayed on the operation panel according to a result of the comparison; and
  disposing and displaying the plurality of operation buttons on the operation panel according to a result of the extraction.

7. A display control method of an operation panel comprising:
  registering a plurality of operation buttons in advance as operation button display conditions, the plurality of operation buttons being displayed on the operation panel when a plurality of controlled instruments satisfy respective predetermined operation state conditions and used to set an operation for each of the plurality of controlled instruments;
  acquiring operation states of the plurality of controlled instruments used in a procedure;
  comparing the operation states with the operation state conditions registered as the operation button display conditions;
  extracting the plurality of operation buttons to be displayed on the operation panel according to a result of the comparison; and
  displaying the plurality of operation buttons side by side in time-series order in a predetermined direction of the operation panel according to a result of the extraction, the operation panel being provided with a plurality of display areas in which the plurality of operation buttons are displayed, respectively.

* * * * *